United States Patent
Liu et al.

(10) Patent No.: US 9,700,724 B2
(45) Date of Patent: Jul. 11, 2017

(54) ELECTRICAL CHARGE BALANCING METHOD AND APPARATUS FOR FUNCTIONAL STIMULATION USING PRECISION PULSE WIDTH COMPENSATION

(71) Applicant: THE REGENTS OF THE UNIVERSITY OF CALIFORNIA, Oakland, CA (US)

(72) Inventors: Wentai Liu, Los Angeles, CA (US); Richard Hill, Los Angeles, CA (US); Yi-Kai Lo, Los Angeles, CA (US); Kuanfu Chen, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/833,115

(22) Filed: Aug. 23, 2015

(65) Prior Publication Data
US 2016/0045743 A1 Feb. 18, 2016

Related U.S. Application Data

(63) Continuation of application No. PCT/US2014/018451, filed on Feb. 25, 2014.
(Continued)

(51) Int. Cl.
*A61N 1/36* (2006.01)
*A61N 1/08* (2006.01)

(52) U.S. Cl.
CPC ....... *A61N 1/36157* (2013.01); *A61N 1/3615* (2013.01); *A61N 1/36032* (2013.01);
(Continued)

(58) Field of Classification Search
CPC ............ A61N 1/36128; A61N 1/36146; A61N 1/36153; A61N 1/36175
See application file for complete search history.

(56) References Cited

U.S. PATENT DOCUMENTS 6,366,813 B1 * 4/2002 DiLorenzo ............. A61B 5/048
607/45
6,553,263 B1 * 4/2003 Meadows .......... A61N 1/36071
607/33

(Continued)

OTHER PUBLICATIONS

Korean Intellectual Property Office (KIPO), International Search Report and Written Opinion, PCT/US2014/018451, Jun. 9, 2014 (pp. 1-13), with claims searched (pp. 14-17), PCT counterpart to the application filed herewith.
(Continued)

*Primary Examiner* — Kennedy Schaetzle
(74) *Attorney, Agent, or Firm* — O'Banion & Ritchey LLP; John P. O'Banion

(57) ABSTRACT

An apparatus and method for electrical charge balancing when generating a stimulus during functional neural stimulation is presented. A stimulus pulse is generated (cathodic or anodic), and after a selected delay a charge compensating pulse is generated of an opposite polarity. The electrode circuit discontinuously examines electrode voltage after termination of the stimulus pulse, and utilizes this voltage to determine how long to extend the width of the charge compensating pulse. The electrode circuit thus performs accurate electrical charge cancellation to remove residual charges from the electrode by precisely controlling pulse width for an opposing polarity compensating pulse that need not have the same current level as the stimulus pulse.

19 Claims, 13 Drawing Sheets

Related U.S. Application Data

(60) Provisional application No. 61/769,524, filed on Feb. 26, 2013.

(52) U.S. Cl.
CPC ..... *A61N 1/36046* (2013.01); *A61N 1/36125* (2013.01); *A61N 1/36142* (2013.01); *A61N 1/36146* (2013.01)

(56) References Cited

U.S. PATENT DOCUMENTS

| | | | |
|---|---|---|---|
| 7,860,570 B2 * | 12/2010 | Whitehurst | ........ A61N 1/37205 607/118 |
| 2002/0077670 A1 | 6/2002 | Archer et al. | |
| 2008/0015641 A1 | 1/2008 | Armstrong et al. | |
| 2010/0152817 A1 | 6/2010 | Gillbe | |
| 2011/0077698 A1 | 3/2011 | Tsampazis | |
| 2011/0125217 A1 | 5/2011 | Carter et al. | |
| 2012/0283800 A1 | 11/2012 | Perryman et al. | |

OTHER PUBLICATIONS

European Patent Office (EPO), Extended European Search Report issued Nov. 4, 2016, related EP Application No. 14756729.1, pp. 1-6, with claims searched, pp. 7-10.

\* cited by examiner

ELECTRICAL CHARGE BALANCING METHOD AND APPARATUS FOR FUNCTIONAL STIMULATION USING PRECISION PULSE WIDTH COMPENSATION

CROSS-REFERENCE TO RELATED APPLICATIONS

This application is a 35 U.S.C. §111(a) continuation of PCT international application number PCT/US2014/018451 filed on Feb. 25, 2014, incorporated herein by reference in its entirety, which claims priority to, and the benefit of, U.S. provisional patent application Ser. No. 61/769,524 filed on Feb. 26, 2013, incorporated herein by reference in its entirety. Priority is claimed to each of the foregoing applications.

The above-referenced PCT international application was published as PCT International Publication No. WO 2014/134075 on Sep. 4, 2014, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to biomedical implantable functional or neural stimulation (FES/FNS), and more particularly to active charge balancing circuits for stimulator circuits.

2. Description of Related Art

Functional electrical stimulation is used in many biomedical implants to restore lost function in individuals by delivering current charge into biological tissues to evoke action potentials. Application examples of this technology include cochlear implants, retinal prosthesis, cortical stimulators, spinal cord implants and deep brain stimulators. These implantable devices typically deliver bi-phasic current to depolarize the neural membrane, aiming to maintain a zero charge residual at the stimulation site.

However, it should be realized that a perfect balance of current pulse amplitude is challenging to achieve due to the intrinsic mismatch of current sink and source drivers (e.g., between 1% and 5%), and interestingly, even with perfectly matched cathodic and anodic current pulses, a condition of zero residual charge is still not achievable due to the inter-pulse delay typically adopted in modern biphasic stimulation.

Numerous methods have been proposed to achieve a safe charge-balanced electrical stimulation. A common passive solution is to insert a DC-blocking capacitor in series with the stimulation electrode. This ensures that only a small DC current (<1 nA) can flow through the electrode. However, to ensure that the voltage drop across the electrode does not significantly increase the compliance voltage required to power the drivers, a physically large capacitor is usually unavoidable. Additionally, one capacitor is required per electrode. It will be appreciated that applying DC-blocking capacitors in a high-density neuron implant, such as a retinal prosthesis, would lead to an overly large physical size that would be impractical for clinical applications.

An alternative passive approach toward achieving charge-balanced stimulation is to short the stimulation electrode to the reference electrode after each stimulation period. This approach can be applied with low-frequency stimulation patterns, however, at high frequency, the time available to discharge the residual charge may be insufficient due to the large capacitance contributed by the reference electrode and usually results in a net DC charge.

Active charge balancing schemes have also been proposed. The pulse insertion technique involves inserting predefined, current pulses at the end of each stimulation pattern. So far, the efficacy of balancing short pulses has not yet been investigated utilizing clinical animal and human tests. There is a possibility that the inserted short pulses might result in unwanted neural responses.

Active offset-cancellation schemes have been similarly proposed. Active offset cancellation is implemented by continuously applying a small DC current to match the anodic and cathodic stimulus, however, a certain amount of settling time is still required for the control loop and inevitably this sets a limitation on stimulation frequency. Furthermore, one principle drawback of this approach is obtaining sufficient resolution of available calibration current, as a more precise calibration current necessitates a more complex hardware implementation.

Accordingly, a need exists for an improved apparatus and method for performing charge balanced functional stimulation. The present invention fulfills that need and overcomes shortcomings of previous functional stimulation implementations.

BRIEF SUMMARY OF THE INVENTION

The present invention is a neural electrode circuit having an electrical charge cancellation scheme to effectively remove residual charge on the electrode by precisely controlling the width of a charge cancelation pulse (either anodic or cathodic). The apparatus and method overcomes many of the shortcomings of previous electrode stimulation designs.

A phenomenon the inventors have observed is that the Faradic charge transfer resistance in the electrode model creates a leakage charge during the period of inter-pulse delay. Thus, previous works which focused on reducing imbalance between cathodic and anodic stimulation current pulses in hopes of reducing residual charges might not be effective ways to ensure a safe neural stimulation. These types of systems typically rely upon the use of additional charge balancing schemes, because a net residual charge can damage surrounding tissue and electrodes due to the toxic electrochemical reaction products, pH changes, gas formation, and electrode dissolution.

In many neural stimulation methods, a substantial emphasis is often placed on creating techniques to improve amplitude matching between cathodic and anodic pulses. However, the inventors have observed that if the Warburg resistance is considered in the electrode model, a net DC voltage will still exist on the electrode even if the cathodic and anodic current amplitudes are matched. The present invention addresses the above shortcomings with these previous neural stimulator systems.

The present invention provides a simple hardware solution that effectively eliminates residual charge for different sink/source mismatches, different electrodes, and variable stimulation amplitudes. Compared to what is known in the art, the present invention achieves increased precision at a lower hardware cost, provides a sufficiently small physical hardware size so as to be surgically implantable, while the system avoids inserting extra pulses that could cause false depolarization of neural membranes.

Several benefits are provided by the present invention, including but not limited to the following. (1) No additional short pulses are required, thus avoiding false depolarization of neural tissue. (2) No DC-blocking capacitor is required for each stimulator, whereby implant size can be reduced. (3) Timing control in the present invention can utilize a portion of existing hardware, such as clock generation hardware, thereby simplifying hardware implementation. (4) The inventive approach provides a high precision mechanism for net charge control. (5) The present invention is still effective at eliminating residual charge even if Warburg resistance is significant.

The invention can be utilized for generating and delivering charge to a stimulator electrode. The inventive apparatus can be programmed to generate different waveforms, and is well-suited for biomedical functional or neural stimulation (FES/FNS) devices. The apparatus can be scaled up to perform charge balanced stimulation for an array of electrodes, as well as, a single electrode.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Figure 1A:
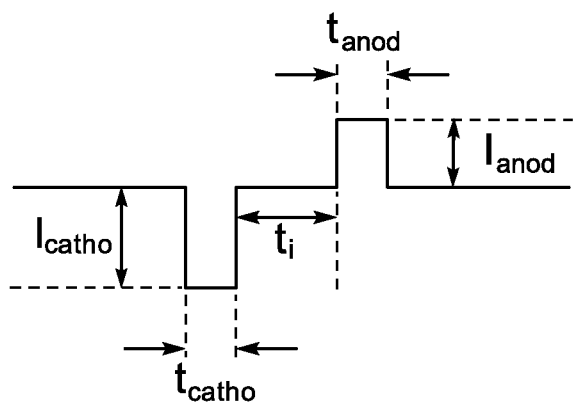
FIG. 1A and FIG. 1B are waveform diagrams of unbalanced current stimulus with equal pulse width (FIG. 1A) and unequal pulse width (FIG. 1B).
Figure 1B:
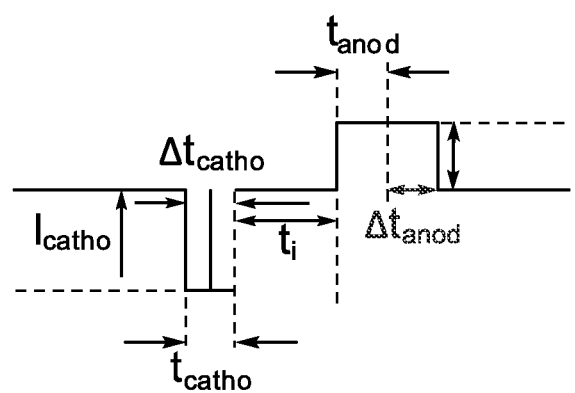

FIG. 1A and FIG. 1B illustrate different unbalanced stimulation current waveforms. In FIG. 1A is seen an unbalanced stimulation current waveform, where $I_{catho}$ and $I_{anod}$ are the amplitude of cathodic and anodic current stimulus, $t_i$ is the inter-phase delay, $t_{catho}$ and $t_{anod}$ are the stimulation pulse widths. It can be seen in FIG. 1A, that the pulse widths of the cathodic and anodic stimulus are the same, while the current levels $I_{catho}$ and $I_{anod}$ are different.

In FIG. 1B, toward achieving a zero net charge residual, the width of anodic/cathodic current stimulus is automatically adapted according to the present invention based on discontinuously sampling stimulus pulse voltage. In one embodiment, a sampling switch, feedback circuit, and digital control circuit are utilized for controlling the width of the compensating pulse generated by a stimulation pulse generator. The present invention allows precise control of these pulse widths and thus accurate charge balancing.

In one embodiment, pulse widths are determined in response to a count of digital pulses from a clock circuit. The present invention allows sharing the use of a clock signal configured for other purposes within the circuit, in particular an implant device. By way of example, one retinal implant utilized a 2 MHz clock, having a clock cycle of 500 ns, to operate its digital controller for commanding the stimulation drivers. Utilizing this example clock signal, with 500 ns clock cycle, the present invention can alter the pulse widths by increments of 500 ns to shorten or prolong stimulus pulse width. If the minimum stimulus current of 3 µA is fired from the electrode, then it will be recognized that the compensation charge delivered is 1.5 pC per 500 ns clock cycle, which is much smaller and thus more precise than the 1.2 nC charge resolution reported for one typical neural stimulator. It should be appreciated that the above clock cycle and current level are provided by way of example and not limitation, as the present invention can be utilized with clock sources across a wide range of frequencies.

For physiological reasons, the leading phase is usually cathodic; although anodic—first pulsing has been explored as a method to more efficiently activate populations of some neural elements. In the cathodic-leading case, the cathodic pulse is intended to stimulate a physiological response, while the anodic pulse is intended to balance the charge. Therefore, in this case, it would be wise to maintain the width of cathodic pulse at excitable levels and to adjust the width of only the anodic phase to compensate, while in the anodic-leading case the opposite would be true. It should be appreciated that schemes involving manipulation of both pulse widths can be implemented following the teachings of the present invention although they are somewhat more complicated.

Figure 2:
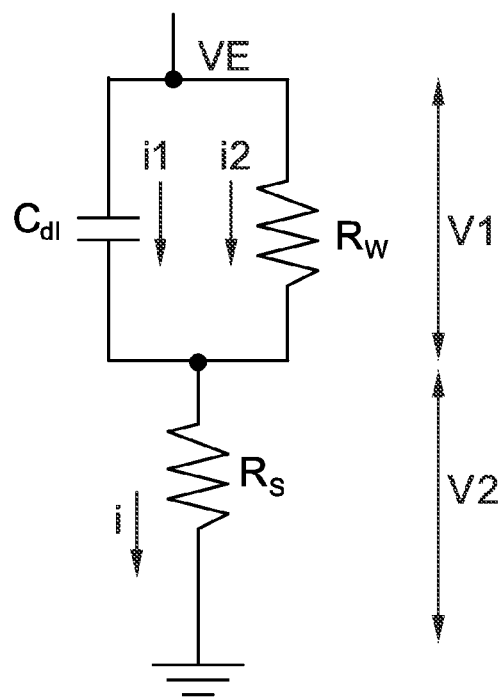
FIG. 2 is a schematic of an electrode model used for the analysis discussed herein.

FIG. 2 depicts a known electrode model that is used in the present analysis, which includes a double layer capacitance of $C_{dl}$, in parallel with a simplified Warburg resistance of $R_W$, the combination of which is in series with a tissue resistance of $R_S$ connected to ground. In response to application of entire voltage $V_E$, a current i1 is seen flowing through $C_{dl}$ and a current i2 is seen flowing through Warburg resistance $R_W$. The voltage drop across the parallel capacitance $C_{dl}$ and resistance $R_W$, is seen as $V_1$, with the drop across tissue resistance $R_S$ seen as $V_2$.

It will be appreciated that elements $C_{dl}$, $R_W$, $R_S$ are part of this universal electrode model, that is described in stimulator publications and textbooks. Utilizing this model, even when the stimulator circuit generates a compensating pulse, it is still difficult to match the amplitude of the compensating pulse to the stimulating pulse. Furthermore, even if one attempts to match these amplitudes, a charge balance still arises if an inter-pulse delay is used in the stimulus pattern, as was described in the background of the invention.

Figure 3:
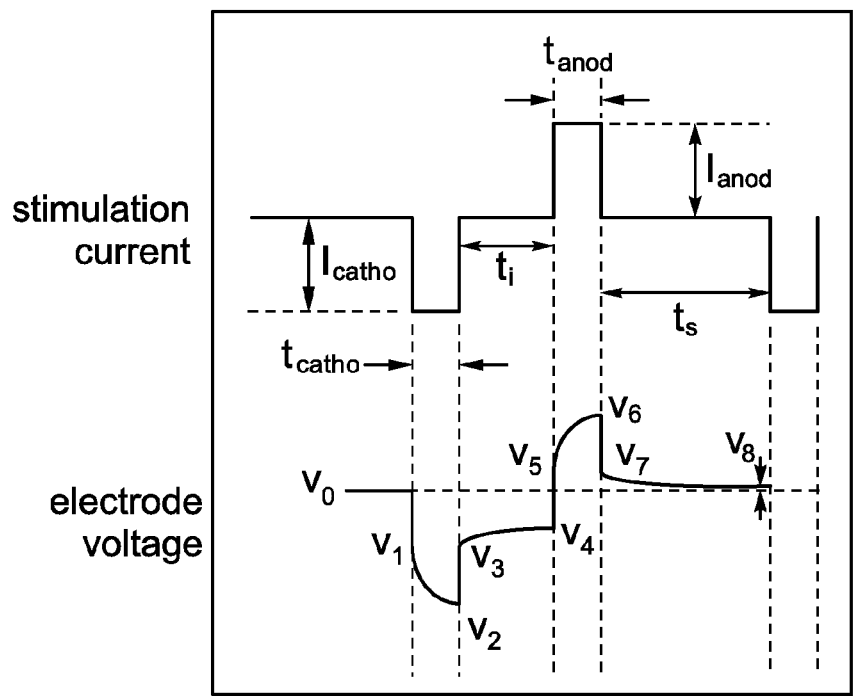
FIG. 3 is a waveform diagram of typical stimulation current and corresponding electrode voltage for the electrode model shown in FIG. 2.

FIG. 3 illustrates a typical stimulation current profile in the upper waveform, along with associated electrode voltage in the lower waveform, which is shown at voltage stations $V_0$ through $V_8$. If a balanced current stimulus is applied, there still remains a net voltage $V_8$ on the electrode after stimulation. The main reason this arises is because $R_w$ creates an addition discharge path during the inter-phase delay $t_i$ and time before next stimulation starts $i_S$. The remaining voltage $V_8$, can be derived as follows:

$$V_8 = \left(I * R_W - V_4 e^{\frac{-t_{anod}}{R_W * C_{dl}}}\right) e^{\frac{-t_S}{R_W * C_{dl}}} \quad (1)$$

where $V_4$ is given by:

$$V_4 = I * R_W \left(1 - e^{\frac{-t_{catho}}{R_W * C_{dl}}}\right) e^{\frac{-t_i}{R_W * C_{dl}}} \quad (2)$$

It can be seen from Eq. (1) that a residual voltage on the electrode exists if $i_s$ is not sufficiently long to discharge the net charge.

Figure 4:
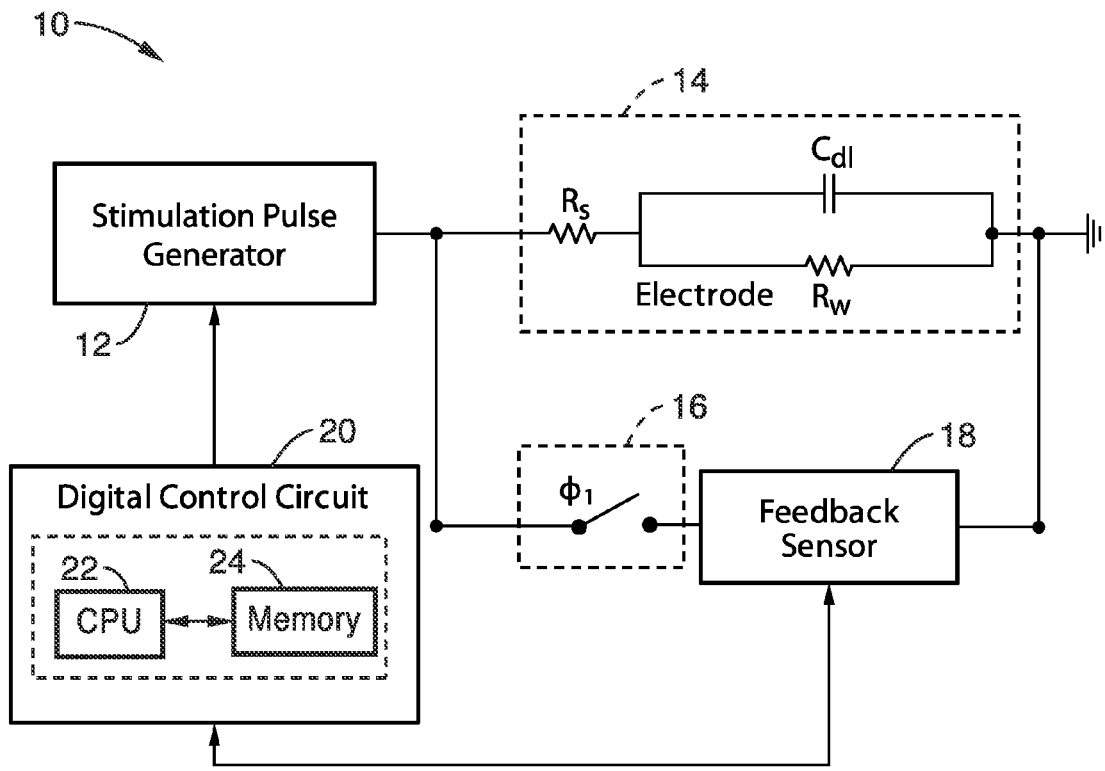
FIG. 4 is a block diagram of a charge cancellation functional stimulation apparatus according to an embodiment of the present invention.

FIG. 4 illustrates an example embodiment 10 of an electrical stimulation device utilizing charge cancellation according to the invention. A stimulation pulse generator 12 is seen outputting stimulation pulses to an electrode 14, which was seen in FIG. 2, with electrode capacitance of $C_{dl}$, Warburg resistance $R_W$, and tissue resistance of $R_S$.

Electrode voltage is sampled discontinuously by turning on/off the φ1 switch 16. The residual voltage is sampled before the next stimulus pulse begins. The timing for obtaining the sampling timing is generated by digital controller circuit 20 since it controls both stimulation pulse generator 12 and feedback sensor 18. Thus, since it is sampled before the next stimulation pulse begins, the inventive circuit can determine the amount of residual voltage, such as seen at the bottom of FIG. 2 depicted as sample $V_8$.

The control circuit in the present invention controls stimulator timing of stimulator, and in particular when to start and when to finish a stimulus pulse. Thus, it is easy for the inventive circuit to precisely sample the residual voltage. A feedback sensor 18 also compares the sampled voltage with a reference and outputs a signal (e.g., trigger) to a digital control circuit 20, which is coupled to stimulation pulse generator 12 for controlling its output. For multi-channel stimulation, the feedback sensor 18 and digital controller 20 can be shared by other electrodes by having multiple φ1 from each electrode connecting to feedback sensor 18, whereby hardware costs can be substantially reduced.

Digital control circuit 20 alters pulse width for a secondary charge balancing pulse, based on input received from the feedback sensor about stimulator output voltage. In at least one embodiment, the pulse width is determined in response to a count of digital pulses, such as from a clock generator circuit, which may be utilized for other purposes within a stimulator circuit. It should be appreciated that digital control circuit 20 can be implemented with various forms of digital control circuitry with volatile or non-volatile memory. a specific pulse width for the compensating pulse is derived, the information of these stimulus parameters can be stored in the memory, such that further computation/power consumption to find the compensating pulse width can be saved once a new stimulus is applied. By way of example and not limitation, a computer processor 22 (e.g., microcontroller) operating in conjunction with a memory 24 (e.g., internal or external to the processor), may be utilized for controlling stimulation pulse generation. The present invention is non-limiting with regard to the memory type utilized insofar as these are non-transitory, and thus not constituting a transitory electronic signal. The use of a processor allows the invention to generate various stimulation regimes, such as different stimulation waveforms. For example, monophasic, symmetric/asymmetric biphasic stimulus, sinusoid, square, and triangular waveforms. Other forms of digital circuitry can be utilized, including logic arrays, gate arrays, field-programmable gate arrays (FPGA), application specific devices (ASICs), other digital control devices, or combinations thereof.

The feedback sensor can be implemented in alternative ways to register stimulator residual voltage without departing from the teachings of the present invention. For example the feedback sensor may comprise either a multiple-bit analog-to-digital converter (ADC) or utilize a comparator. Considering the case where the feedback sensor generates a trigger pulse if a positive residual voltage exceeds a value of $V_{ref}$ then the digital control circuit responds by increasing width of cathodic current pulse, or decreasing the width of the anodic current pulse. Similarly, a trigger is generated when the absolute value of the negative residual voltage exceeds $V_{ref}$.

Figure 5A:
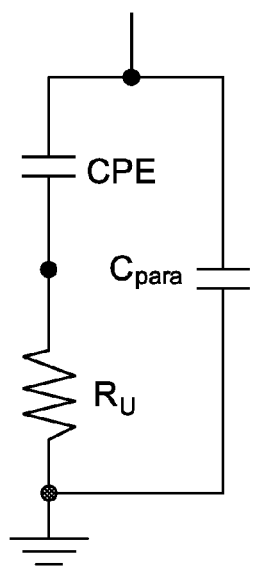
FIG. 5A and FIG. 5B are two different electrode models utilized according to embodiments of the present invention for verifying charge cancellation.
Figure 5B:
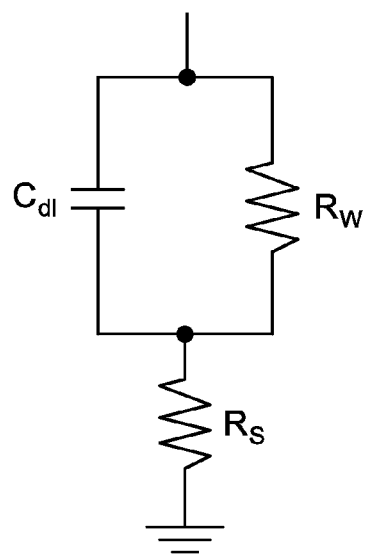

FIG. 5A and FIG. 5B illustrate two separate electrodes upon which simulations were performed according to the invention. The electrode of FIG. 5A is based on an electrode model utilized to simulate a retina prosthesis, with tissue resistance $R_u$ as 31 kΩ, the constant phase element (CPE), (e.g., modeled as a capacitor for simplicity of illustration) was simplified to a 100 nF capacitor, while a parasitic capacitance $C_{parasitic}$ is exemplified as 105 nF. The electrode of FIG. 5B is a three-element model as shown in FIG. 2, emphasizing the Warburg impedance.

A version of Simulink® models was used for simulating electrical charge balancing according to the invention. In this implementation, a proportional-integral-derivative controller (PID controller) was utilized in the digital control circuit. PID coefficients were determined using rule-based tuning schemes. The Classic Ziegler-Nichols method showed the best disturbance rejection for most scenarios. For all mismatches, the rule-based parameters were roughly $K_p$=3.6E-4, $K_i$=4.5 E-3, and $K_d$=3.84 E-6. However, for comparator based schemes, $K_d$ was set to 0. In this model, the width of the anodic phase is adjustable between 0.7 ms and 1.4 ms.

Simulink® simulations were also performed to assess the charge cancellation scheme for different sink/source mismatches, different electrodes, variable amplitudes, and different hardware implementations. Simulation parameters were based on a retinal prosthesis chip. For a 100 µm×100 µm platinum alloy electrode, there is a safe electric potential operation range between −0.6 and 0.8 V, limited mostly by the reduction/oxidation of water.

Figure 6:
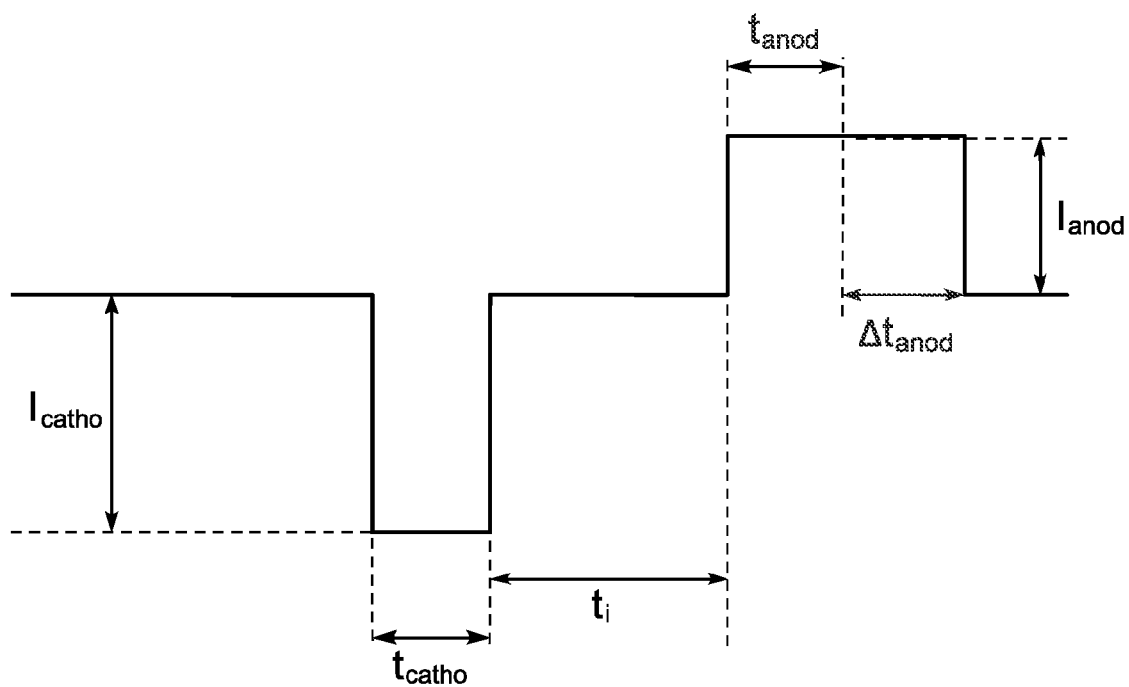
FIG. 6 is a waveform diagram of simulating a bi-phasic pulse waveform according to an embodiment of the present invention.

FIG. 6 depicts bi-phasic, cathodic-leading pulses for electrode stimulation. The inter-phase delay $t_i$ is 1 ms, with $t_{catho}$ at 1 ms, and $t_{anod}$ is adjustable between 0.7 and 1.4 ms (starting at 1 ms). The period of the waveform is 0.02 seconds (20 ms). The pulses had base amplitude of 200 µA. The scheme was tested with various scenarios: (a) Cathodic +15% in which a cathodic amplitude of 230 µA and anodic amplitude of 200 µA. (b) Cathodic +5%, Cathodic −5%, Cathodic −15%, Anodic +15%, Anodic +5%, Anodic −5%, Anodic −15%, and no mismatch.

Aside from various mismatch scenarios discussed above, the present invention was further tested with different hardware implementations, in which the amplitude of the stimulation was either fixed over time or the amplitude changed randomly over time, with the same percentage of mismatch. The variable amplitude is more similar to an application in a retinal or cochlear implant, where the amplitude of stimulation will constantly vary according to the image/audio perceived.

Furthermore, different measurement precisions for the resting voltage were used. Proof of concept was determined by simply passing the output of the electrode transfer function, which performs like a very floating point ADC. Further tests were performed with a 4 bit ADC and a comparator. PID Control was used to precisely control the width of the anodic pulse FIG. 7 through FIG. 14 show the results of testing with the electrode model that emphasized Warburg resistance. This charge cancellation scheme was effective for all mismatches tested, which includes mismatches larger than normally experienced.

FIG. 7 through FIG. 15 depict various simulation results for the present invention.

Figure 7:
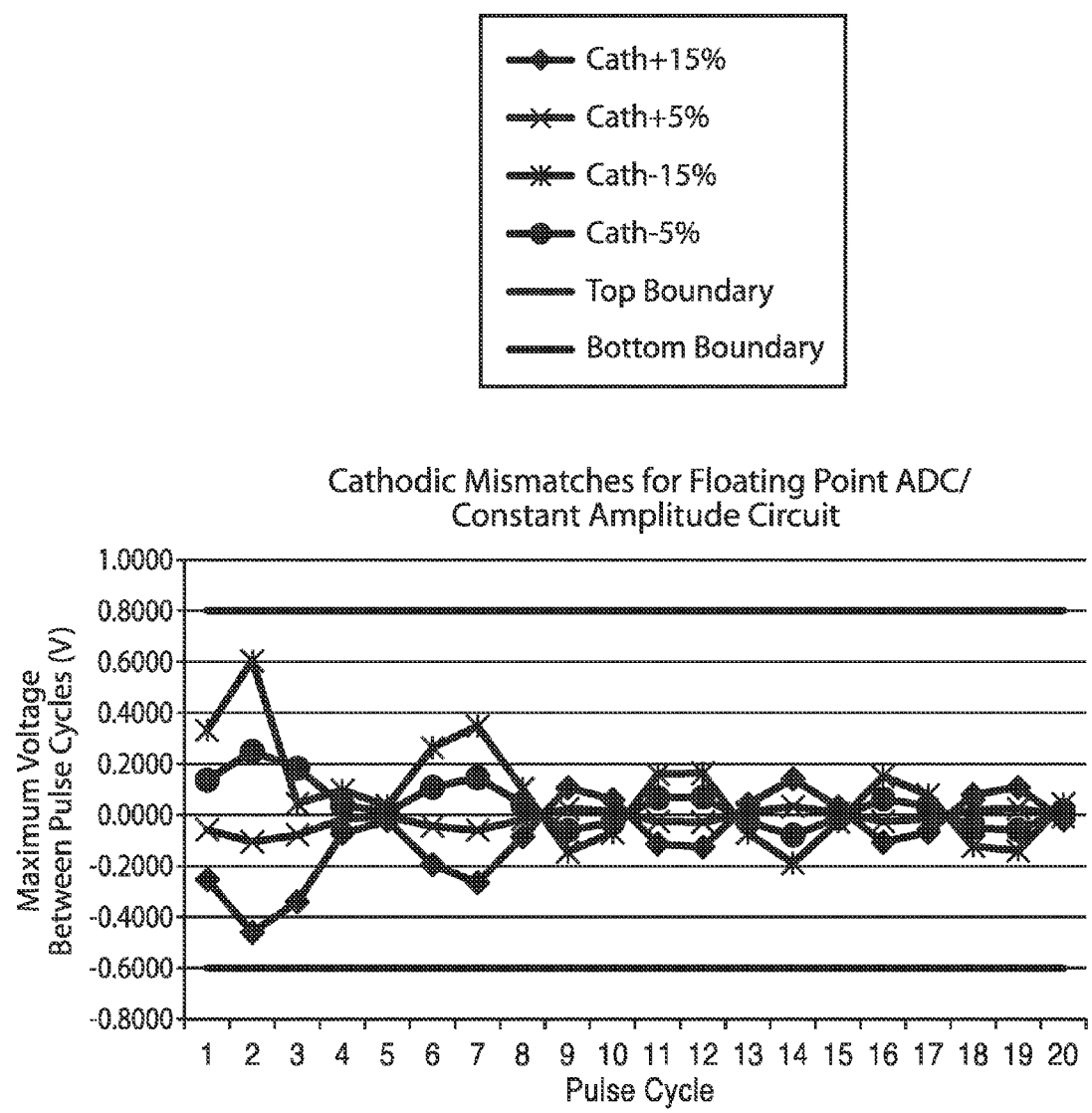
FIG. 7 and FIG. 8 are plots of cathodic mismatches for floating point analog-to-digital conversion in a corrected/non-corrected, respectively, constant amplitude circuit according to a simulation of an embodiment of the present invention.
Figure 8:
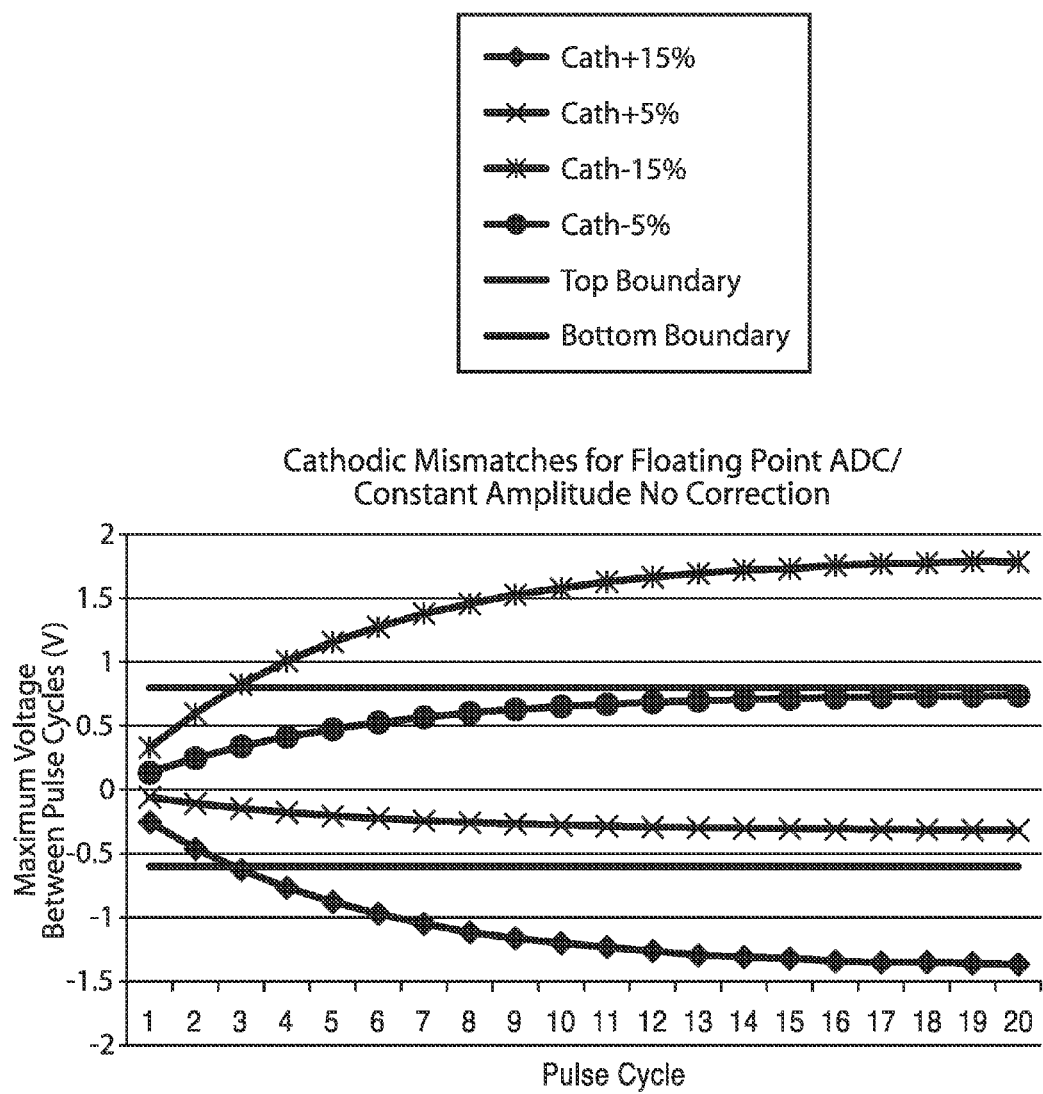
Figure 9:
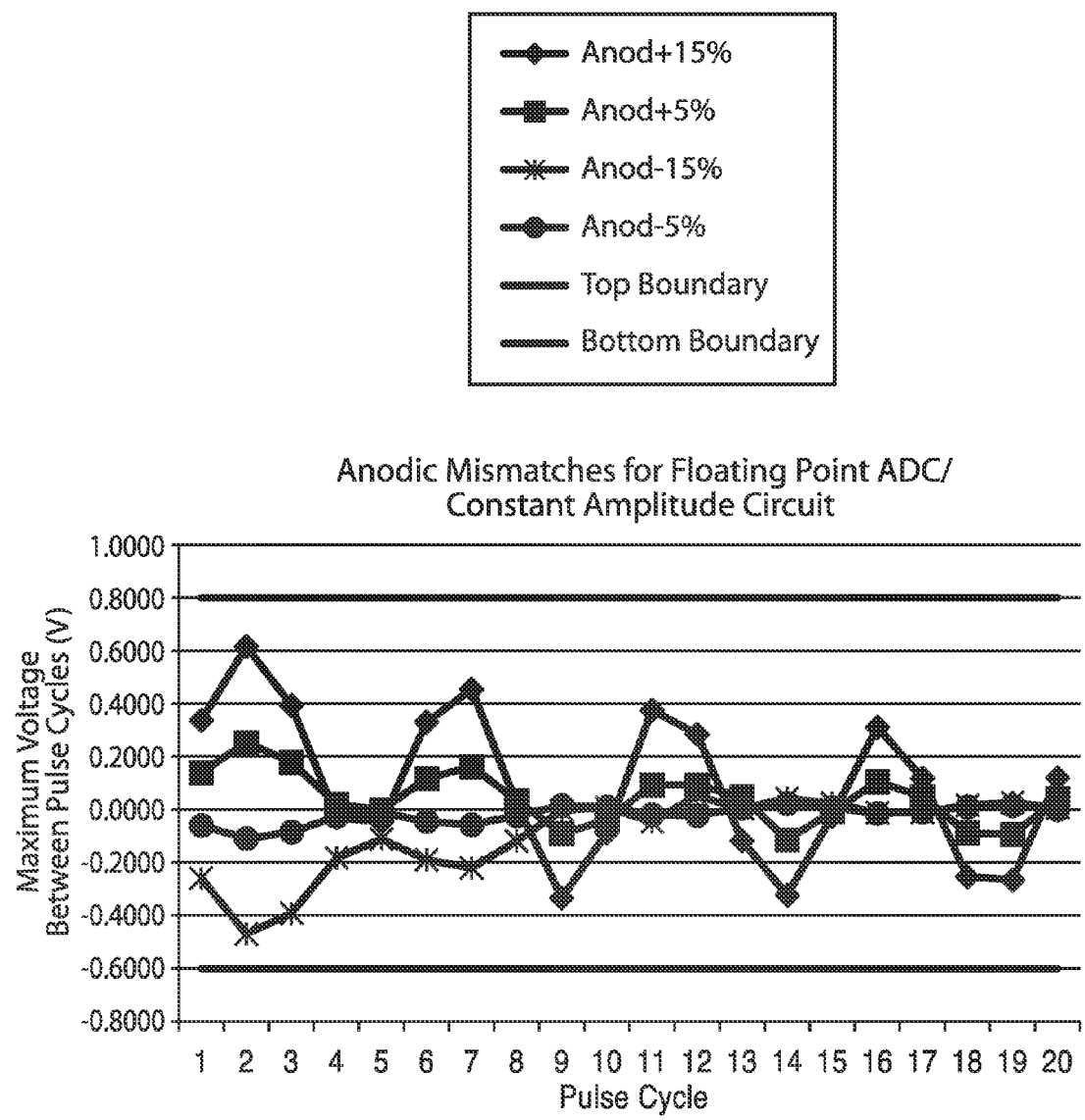
FIG. 9 and FIG. 10 are plots of anodic mismatches for floating point analog-to-digital conversion in a corrected/non-corrected, respectively, constant amplitude circuit according to a simulation of an embodiment of the present invention.
Figure 10:
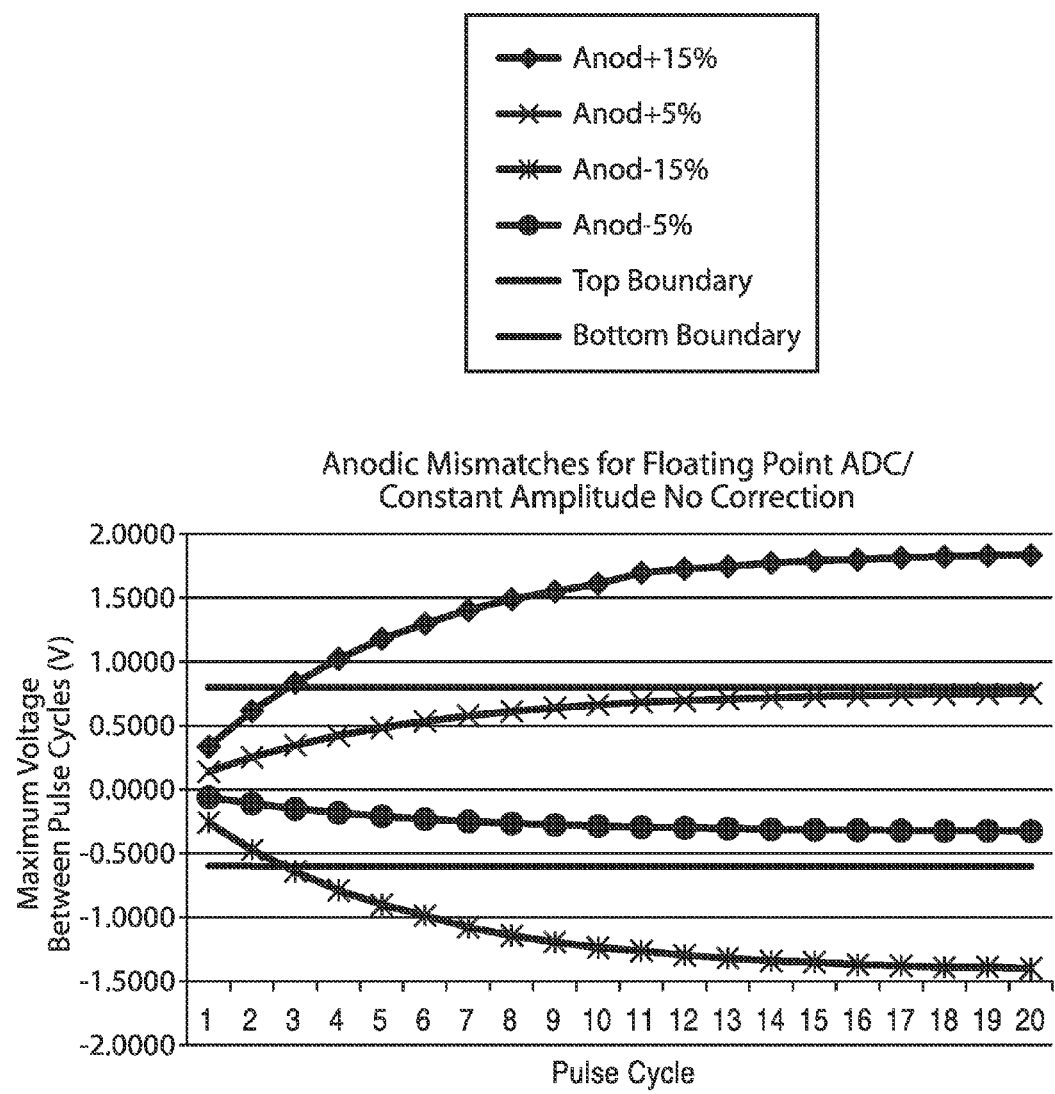

In FIG. 7 and FIG. 8 are seen simulation results of cathodic mismatches for floating point analog-to-digital conversion in a corrected (FIG. 7), and non-corrected (FIG. 8), constant amplitude circuit of the present invention In FIG. 9 and FIG. 10 are seen simulation results of anodic mismatches for floating point analog-to-digital conversion in a corrected (FIG. 9), and non-corrected (FIG. 10), constant amplitude circuit of the present invention.

It should be recognized that FIG. 7 through FIG. 10 demonstrate the effectiveness of the proposed charge cancellation scheme when fixed stimulus intensities with different mismatch ratios are applied. Note that without correction, using a larger stimulus current with fixed mismatch results in a larger residual voltage.

Figure 11:
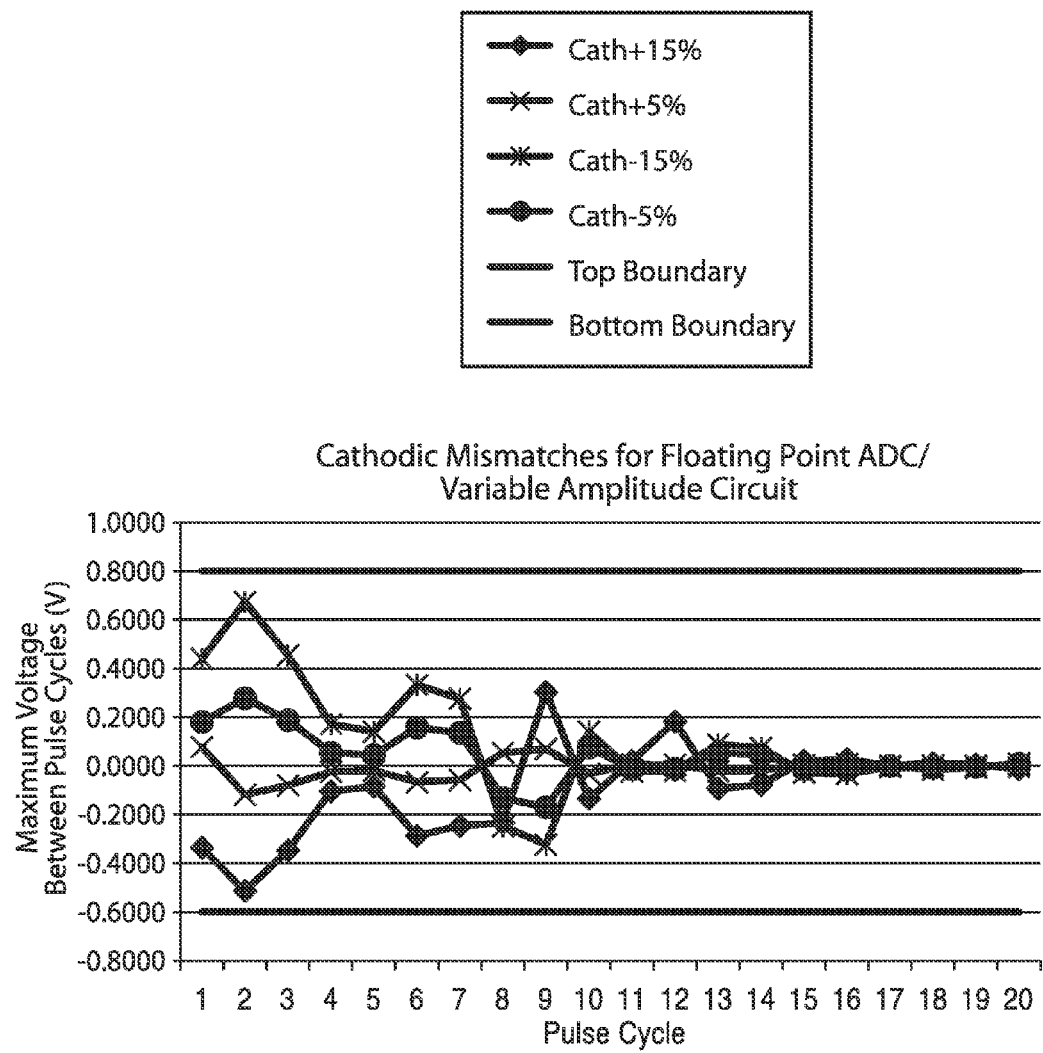
FIG. 11 and FIG. 12 are plots of cathodic mismatches for floating point analog-to-digital conversion in a corrected/non-corrected, respectively, variable amplitude circuit according to a simulation of an embodiment of the present invention.
Figure 12:
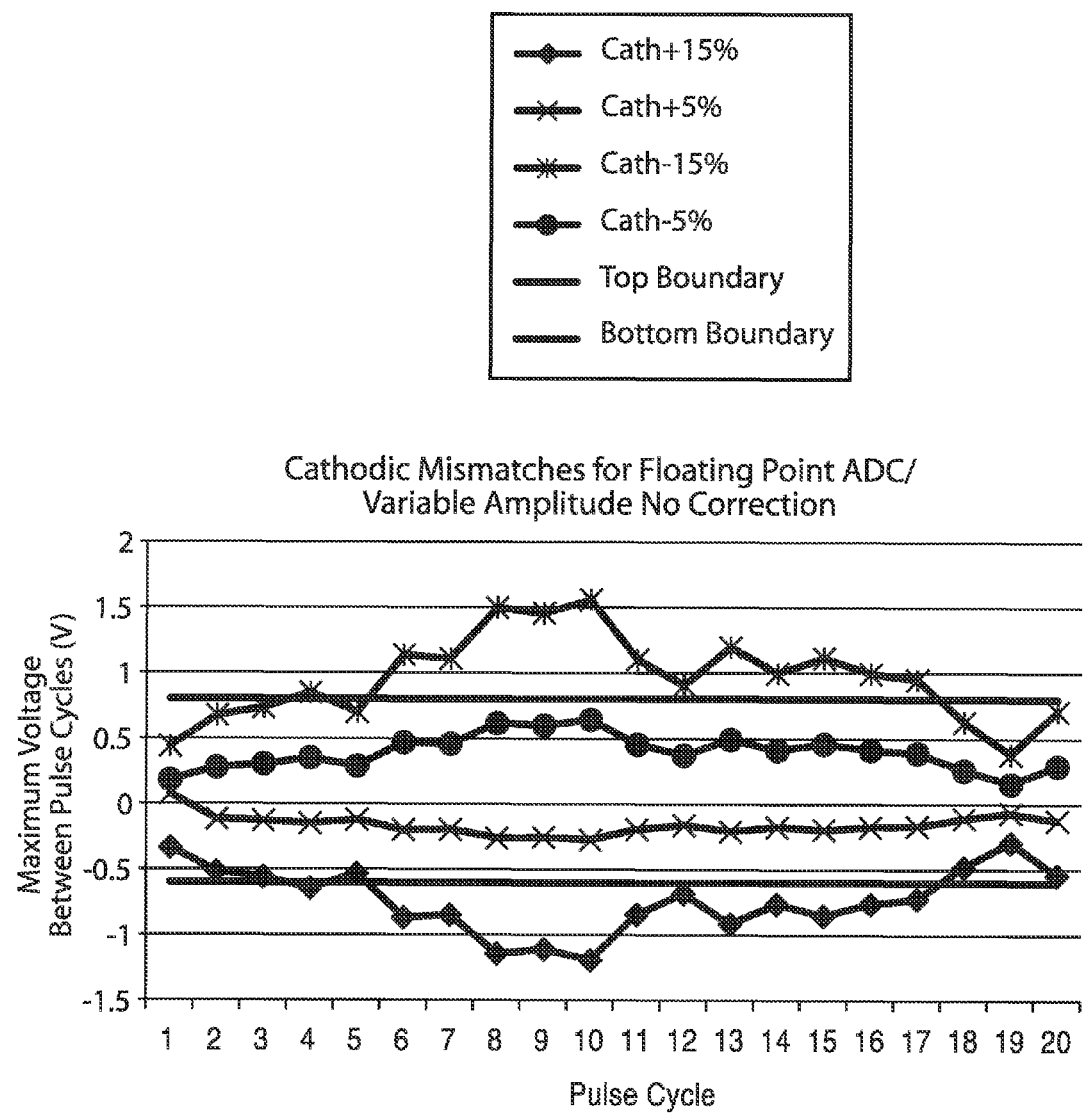

In FIG. 11 and FIG. 12 are seen simulation results of cathodic mismatches for floating point analog-to-digital conversion in a corrected (FIG. 11), and non-corrected (FIG. 12), variable amplitude circuit of the present invention.

Figure 13:
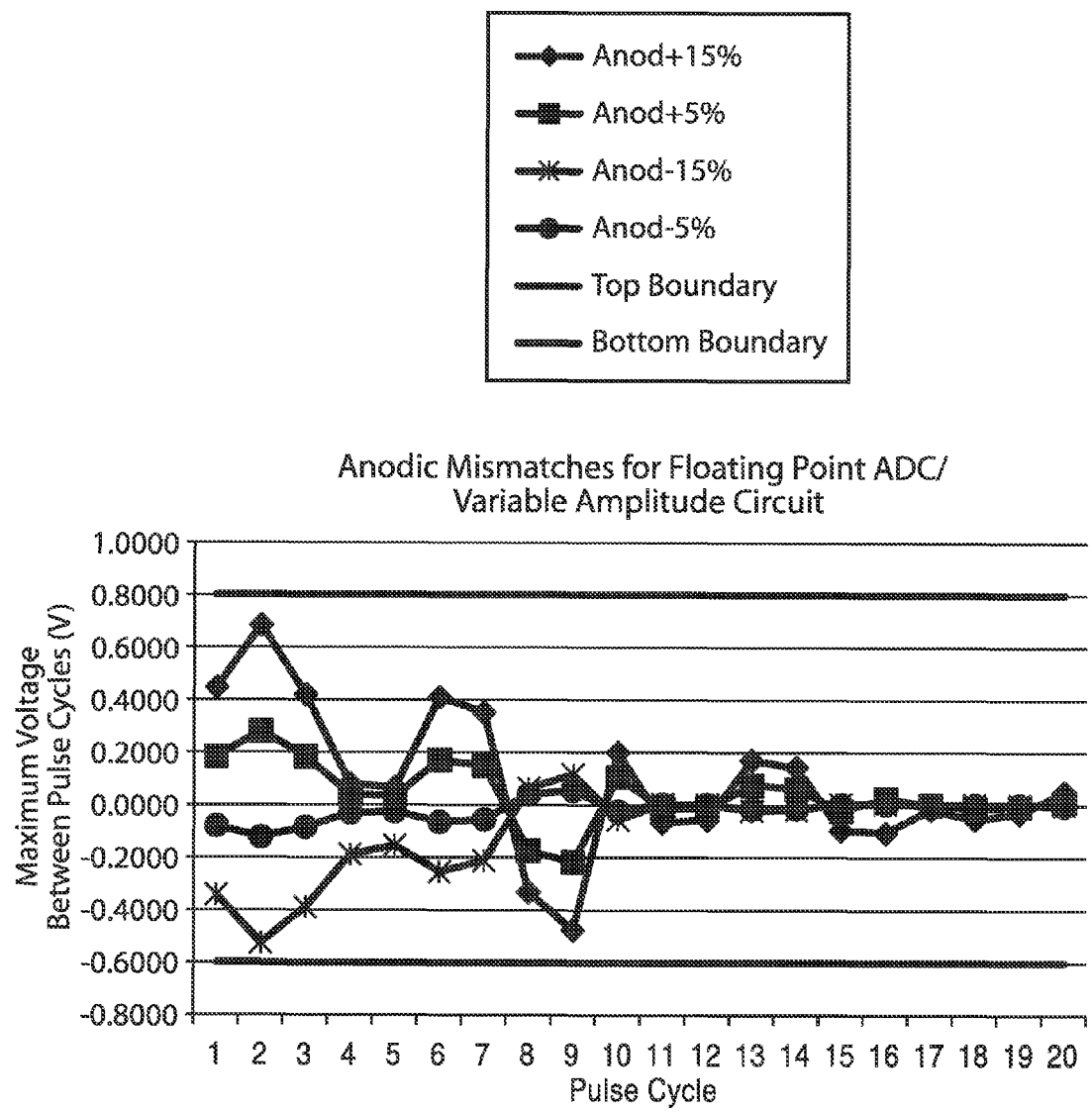
FIG. 13 and FIG. 14 are plots of anodic mismatches for floating point analog-to-digital conversion in a corrected/non-corrected, respectively, variable amplitude circuit according to a simulation of an embodiment of the present invention.
Figure 14:
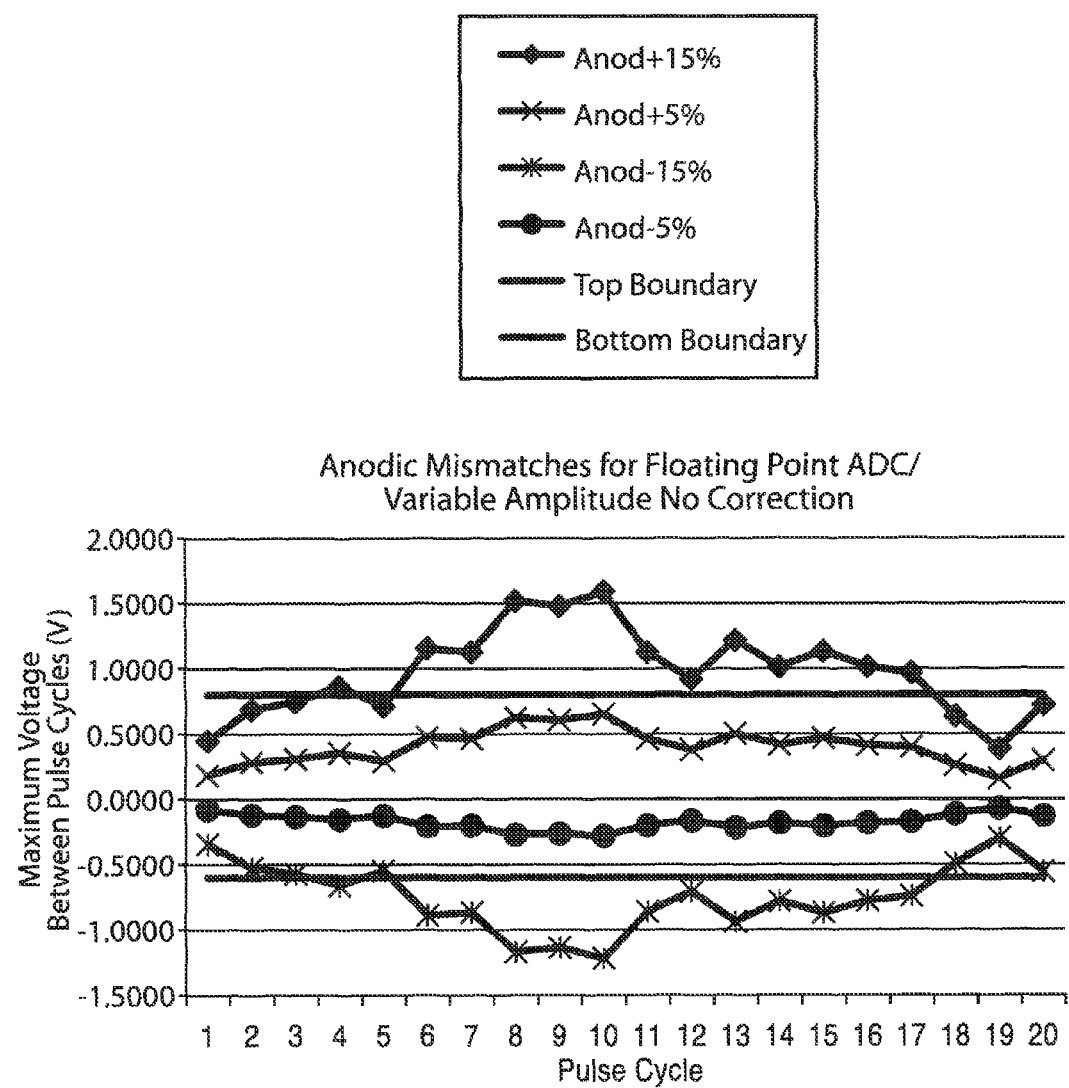

In FIG. 13 and FIG. 14 are seen simulation results of anodic mismatches for floating point analog-to-digital conversion in a corrected (FIG. 13), and non-corrected (FIG. 14), variable amplitude circuit of the present invention. It should be recognized that FIG. 11 to FIG. 14 demonstrate that even for stimulus with varying intensity (e.g., a retinal prostheses in which stimulus patterns are constantly changing depending on environment of the subject). The proposed scheme can still effectively reduce residual voltage.

Figure 15:
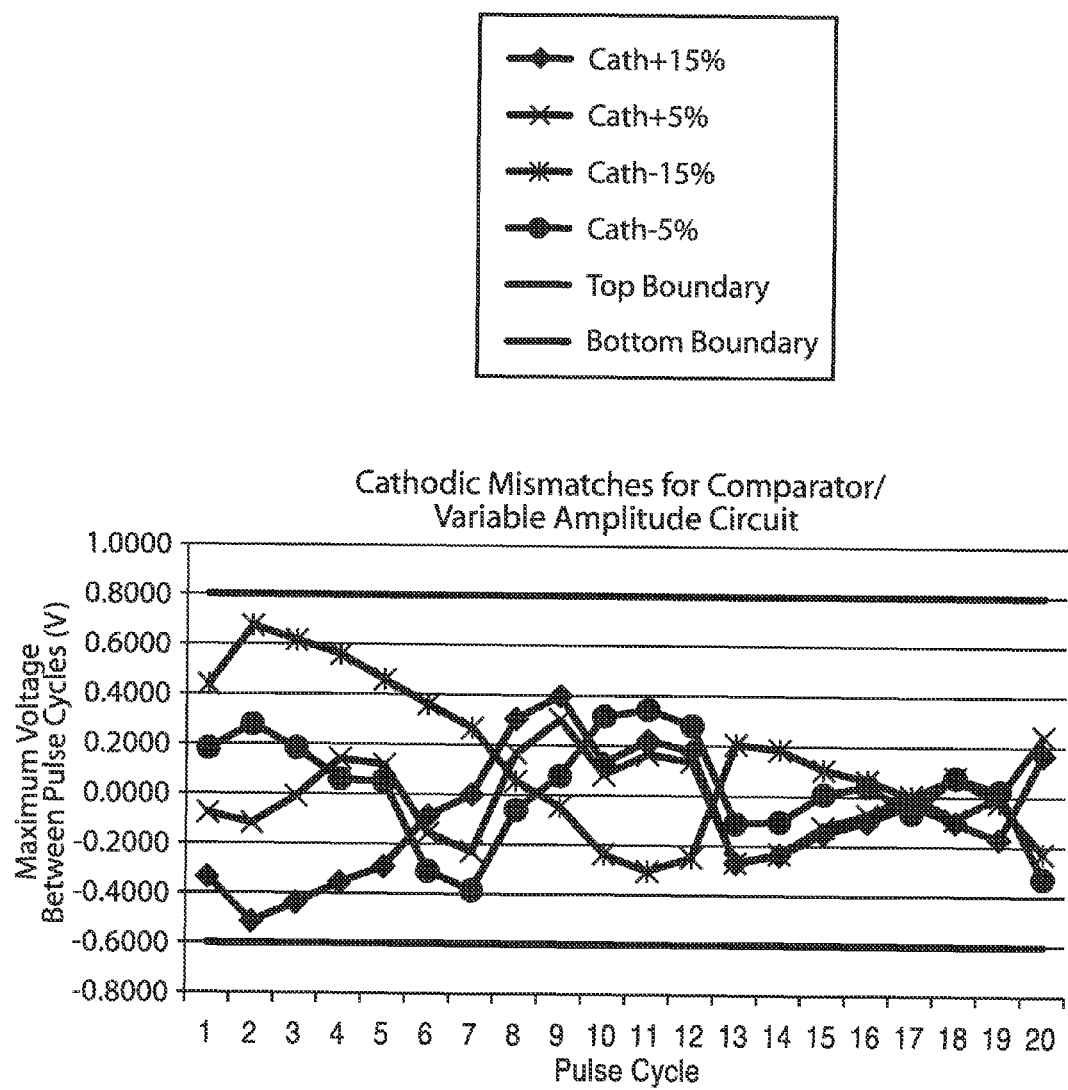
FIG. 15 is a plot of cathodic mismatches for the comparator/variable amplitude circuit according to a simulation of an embodiment of the present invention.

In FIG. 15 is shown a plot of cathodic mismatches for the inventive comparator/variable amplitude circuit.

Additional results of the present invention indicated that the apparatus was effective using a comparator instead of high-bit ADC. Furthermore, the scheme was sufficiently robust to perform well for a retinal prosthesis design where the amplitude of the stimulation pulses is variable to the input.

As has been seen throughout these discussions, the present invention provides a novel charge cancellation mechanism to effectively remove residual net charge. The stimulus pulse can be fine-tuned during each stimulation cycle such that a long passive discharge time and additional compensating pulse(s), or DC-blocking capacitors, are unnecessary. The invention thus overcomes many of the shortcomings of existing neural stimulation devices.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart (s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including but not limited to the following:

1. An apparatus for electrical charge balancing when generating functional neural stimulation, comprising: one or more stimulus electrodes; a stimulation pulse generation circuit configured for driving current waveforms as a cathodic or anodic stimulus through said one or more stimulation electrodes; a switching circuit configured for sampling electrode voltage from each said stimulus electrode when each stimulus terminates; a feedback sensor coupled to said switching circuit for generating triggering signals in response to comparing electrode voltage sampled by said switching circuit with a reference; and a digital control circuit configured for causing said stimulation pulse generation circuit to output a either a cathodic or anodic stimulus pulse, then after a selected delay causing said stimulation pulse generation circuit to generate an opposing polarity pulse having a pulse width that is adjusted by said digital control circuit toward achieving a zero net charge residual based on input from said trigger signals.

2. The apparatus of any of the previous embodiments, wherein said one or more stimulus electrodes comprises an array of electrodes.

3. The apparatus of any of the previous embodiments, wherein said switching circuit is configured for turning on and off a switch to discontinuously connect voltage from the stimulation electrode to said feedback sensor when each stimulus pulse terminates.

4. The apparatus of any of the previous embodiments, wherein said feedback sensor comprises a multiple-bit analog-to-digital converter (ADC).

5. The apparatus of any of the previous embodiments, wherein said feedback sensor comprises a comparator.

6. The apparatus of any of the previous embodiments, wherein said feedback sensor generates to a trigger to said digital control circuit in response to comparing stimulation electrode voltage with a reference voltage.

7. The apparatus of any of the previous embodiments, wherein if a positive residual voltage is larger than a positive reference voltage, then width of cathodic current in said opposing polarity pulse is increased, or alternatively width of anodic current in said opposing polarity pulse is decreased.

8. The apparatus of any of the previous embodiments, wherein if a negative residual voltage is less than a negative reference voltage, then width of cathodic current in said opposing polarity pulse is increased, or alternatively width of anodic current in said opposing polarity pulse is decreased.

9. The apparatus of any of the previous embodiments, wherein said digital control circuit is configured to control the width of the opposing polarity pulse in response to a count of periods from a digital clock circuit, toward providing precision pulse width compensation.

10. The apparatus of any of the previous embodiments, wherein digital control circuit is configured to allow a selection of different stimulation waveforms.

11. The apparatus of any of the previous embodiments, wherein said apparatus does not require matching opposing pulse amplitudes toward achieving charge-balanced electrical stimulation.

12. The apparatus of any of the previous embodiments, wherein said apparatus does not insert extra pulses, beyond said opposing polarity pulse, to achieve zero net charge residual, as these extra pulses can cause false depolarization of neural membranes.

13. The apparatus of any of the previous embodiments, wherein said stimulus electrodes do not incorporate a DC-blocking capacitor in series with each stimulator to reduce DC current.

14. The apparatus of any of the previous embodiments, wherein said apparatus overcomes problems with leakage charge during inter-pulse delay periods that arise in response to Faradic charge transfer resistance of an electrode.

15. The apparatus of any of the previous embodiments, wherein said stimulus and said opposing polarity pulse are not limited to having matched cathodic and anodic current.

16. The apparatus of any of the previous embodiments, wherein said stimulus and said opposing polarity pulse differ to support generation of electrode stimulation patterns having unmatched cathodic and anodic current intensity.

17. The apparatus of any of the previous embodiments, wherein said apparatus is integrated within a biomedical implantable functional or neural stimulation (FES/FNS) device.

18. The apparatus of any of the previous embodiments, wherein said apparatus is integrated within a biomedical implant device selected from the group of implant devices consisting of cochlear implants, retinal prosthesis, cortical stimulators and deep brain stimulators.

19. A method for electrical charge balancing of functional neural stimulation, comprising: generating a stimulus pulse; examining electrode voltage discontinuously by turning an on/off a switch for sampling electrode voltage when each stimulus pulse terminates; comparing the electrode voltage being sampled against a reference voltage to trigger a digital control circuit; and changing pulse width of an opposite polarity pulse, configured for charge compensation of said stimulus pulse, in response to comparing said sampled voltage with said reference voltage.

20. The method of any of the previous embodiments, wherein comparing of the electrode voltage is performed utilizing a multiple-bit analog-to-digital converter (ADC) or a comparator.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for electrical charge balancing when generating functional neural stimulation, comprising:
    (a) one or more stimulus electrodes;
    (b) a stimulation pulse generation circuit having a current sink and a current source, with said stimulation pulse generation circuit configured for directly driving current waveforms, without passing through a blocking capacitor, as a bi-phasic stimulus having both a cathodic and anodic phase through a single stimulus electrode within said one or more stimulus electrodes;
    (c) a switching circuit configured for sampling electrode voltage from each said stimulus electrode when each bi-phasic stimulus terminates with residual voltage sampled before the next stimulus pulse begins;
    (d) a feedback sensor coupled to said switching circuit for generating triggering signals in response to comparing electrode voltage sampled by said switching circuit with a reference; and
    (e) a digital control circuit coupled to said switching circuit and configured for receiving said feedback sensor triggering signals from said feedback sensor, said digital control circuit is configured for performing steps comprising:
        (i) causing said stimulation pulse generation circuit to output a bi-phasic stimulus having a first phase pulse as either a cathodic or anodic stimulus pulse;
        (ii) causing said stimulation pulse generation circuit to generate a second phase pulse as an opposing polarity pulse after a selected delay from said first phase pulse;
        (iii) adjusting pulse width of said first phase pulse and/or second phase pulse based on measured charge imbalance from residual charge measurements on a previous bi-phasic stimulus toward achieving a zero net charge residual based on input from said triggering signals to provide an equal electrical charge in each stimulation phase; and
        (iv) detecting stimulation charge imbalance by directly measuring electrode residual voltage from said stimulus electrode, without using a voltage measurement resistor across which voltage is sensed.

2. The apparatus recited in claim 1, wherein said one or more stimulus electrodes comprises an array of electrodes.

3. The apparatus recited in claim 1, wherein said switching circuit is configured for turning on and off a switch to discontinuously connect voltage from the stimulation electrode to said feedback sensor when each stimulus pulse terminates.

4. The apparatus recited in claim 1, wherein said feedback sensor comprises a multiple-bit analog-to-digital converter (ADC).

5. The apparatus recited in claim 1, wherein said feedback sensor comprises a comparator.

6. The apparatus recited in claim 1, wherein said feedback sensor generates a trigger to said digital control circuit in response to comparing stimulation electrode voltage with a reference voltage to control the output of said stimulation pulse generation circuit.

7. The apparatus recited in claim 6, wherein if a positive residual voltage is larger than a positive reference voltage, then width of cathodic current in said opposing polarity pulse is increased, or alternatively width of anodic current in said opposing polarity pulse is decreased.

8. The apparatus recited in claim 6, wherein if a negative residual voltage is less than a negative reference voltage, then width of cathodic current in said opposing polarity pulse is increased, or alternatively width of anodic current in said opposing polarity pulse is decreased.

9. The apparatus recited in claim 1, further comprising a digital clock circuit coupled to said digital control circuit which is configured to control the width of said first phase pulse and/or second phase pulse in response to a count of periods from said digital clock circuit, toward providing precision pulse width compensation.

10. The apparatus recited in claim 1, wherein digital control circuit is configured to allow a selection of different stimulation waveforms.

11. The apparatus recited in claim 1, wherein said digital control circuit is configured for generating said first phase pulse and/or second phase pulse with an adjustable width, whereby said control circuit does not require matching opposing pulse amplitudes toward achieving charge-balanced electrical stimulation.

12. The apparatus recited in claim 1, wherein said digital control circuit is configured for generating said first phase pulse and/or second phase pulse with an adjustable width to arrive at a zero net charge residual, whereby said control circuit does not insert extra pulses, beyond said opposing polarity pulse, to achieve zero net charge residual, as these extra pulses can cause false depolarization of neural membranes.

13. The apparatus recited in claim 1, wherein said stimulus electrodes are directly coupled to said stimulation pulse generation circuit, and thus do not incorporate a DC-blocking capacitor in series with each stimulus electrode to reduce DC current.

14. The apparatus recited in claim 1, wherein said digital control circuit is configured for generating said first phase pulse and/or second phase pulse having pulse widths to arrive at a zero net charge residual, whereby stimulus and said opposing polarity pulse are not limited to having matched cathodic and anodic current.

15. The apparatus recited in claim 14, wherein said digital control circuit is configured for generating said stimulus and said opposing polarity pulse which differ to support generation of electrode stimulation patterns having unmatched cathodic and anodic current intensity.

16. The apparatus recited in claim 1, wherein said apparatus is configured for integration within a biomedical implantable functional or neural stimulation device.

17. The apparatus recited in claim 1, wherein said apparatus is configured for integration within a biomedical implant device selected from the group of implant devices consisting of cochlear implants, retinal prosthesis, cortical stimulators and deep brain stimulators.

18. A method for electrical charge balancing of functional neural stimulation, comprising:

(a) generating a bi-phasic stimulus pulse in response to current sinking and current sourcing so that said bi-phasic stimulus pulse has both a cathodic and anodic phase;

(b) coupling said bi-phasic stimulus pulse directly to a single stimulus electrode, without passing through a blocking capacitor;

(c) examining electrode voltage discontinuously by turning on/off a switch for sampling electrode voltage when each bi-phasic stimulus terminates with residual voltage sampled before the next stimulus pulse begins;

(d) comparing the electrode voltage being sampled against a reference voltage to trigger a digital control circuit; and (e) changing pulse width of said first phase pulse and/or second phase pulse based on measured charge imbalance from residual charge measurements on a previous bi-phasic stimulus, configured for charge compensation of said stimulus pulse, in response to comparing said sampled voltage with said reference voltage to provide an equal electrical charge in each stimulation phase; and (f) detecting stimulation charge imbalance by directly measuring electrode residual voltage, without using a voltage measurement resistor across which voltage is sensed.

19. The method recited in claim 18, wherein comparing of the electrode voltage is performed utilizing a multiple-bit analog-to-digital converter (ADC) or a comparator.

* * * * *